United States Patent
O'Lenick, Jr.

(10) Patent No.: US 7,632,488 B1
(45) Date of Patent: Dec. 15, 2009

(54) CROSSLINKED SILICONE POLYMERS

(76) Inventor: Anthony John O'Lenick, Jr., 2170 Luke Edwards Rd., Dacula, GA (US) 30019

( * ) Notice: Subject to any disclaimer, the term of this patent is extended or adjusted under 35 U.S.C. 154(b) by 888 days.

(21) Appl. No.: 11/335,718

(22) Filed: Jan. 20, 2006

(51) Int. Cl.
*A61K 5/12* (2006.01)
(52) U.S. Cl. ..................................... 424/70.12
(58) Field of Classification Search ............... 424/70.12
See application file for complete search history.

(56) References Cited

U.S. PATENT DOCUMENTS 6,139,823 A   10/2000   Drechler et al.

*Primary Examiner*—Michael G. Harley
*Assistant Examiner*—James Rogers

(57) ABSTRACT

The present invention relates to a series of crosslinked silicone polymers that by virtue of the nature of the dimol alcohol undecylenic acid ester based crosslinker, have unique solubility and properties. These include improved tolerance for oily materials and improved skin feel. These polymers find use in personal care applications like pigmented products. In the personal care arena, solid products that do not experience syneresis are important. Syneresis is a condition that exists in a solid product that causes a liquid that is incompatible to ooze out, which is cosmetically unacceptable.

20 Claims, No Drawings

CROSSLINKED SILICONE POLYMERS

FEDERAL SPONSORSHIP

None

FIELD OF THE INVENTION

The present invention relates to a series of crosslinked silicone polymers that by virtue of the nature of the crosslinker have unique solubility and properties. These include improved tolerance for oily materials and water soluble materials. These polymers find use in personal care applications like pigmented products. In the personal care arena, solid products that do not experience syneresis are important. Syneresis is a condition that exists in a solid product that causes a liquid that is incompatible to ooze out, which is cosmetically unacceptable.

BACKGROUND OF THE INVENTION

The term silicone resin has been applied both to and misapplied to a variety of materials over time. Silicone resins as used herein refer to a series of products which include at least two silicone backbones that are joined by a "crosslinking group". The number of crosslinking groups that are present as a percentage of the total molecular weight will determine the properties of the resulting polymer.

If there are no crosslinking groups; the polymer can freely rotate and consequently is an oily liquid. If a few crosslinking groups are introduced, the ability to rotate is slightly restricted and the oily material becomes "rubbery". The rubbery material should be referred to as an elastomer. The properties are morel like a rubber band than plastic. As the percentage of crosslinking increases still the molecule becomes rigid. This class of compounds are resins. If you hit the film with a hammer and it shatters it is a resin, if it bounces it is an elastomer and if it squirts out is a silicone fluid.

The difficulty in determining if a product is a fluid an elastomer or resin occurs for products that lie between the classifications. Specifically, when does an elastomer become a resin? While this exact point is of academic interest it does not have any practical significance to the present invention.

There are a number of classes of resin compounds differing in the nature of the crosslinker. One class is the so called "Q resins".

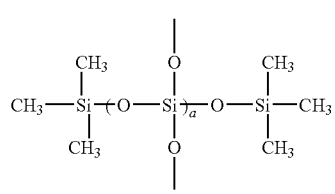

The oxygen that needs another bond connects to another polymer as shown:

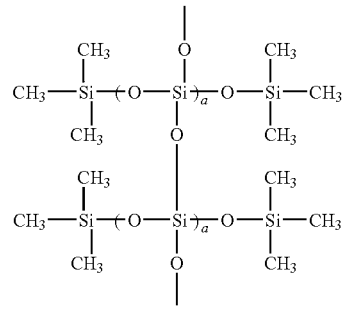

The crosslinking group is —O—. This type of resin is disclosed in U.S. Pat. No. 6,139,823, incorporated herein by reference. This type of material has a group, the so called "Q" group in which a Si has four oxygen atoms attached. In the above case it is the group that is within the "a" subscript. This type of resin is very powdery and is rarely used without a plasticizer. This class of compounds can also dry the skin.

The next class of resin contain alkyl connecting groups.

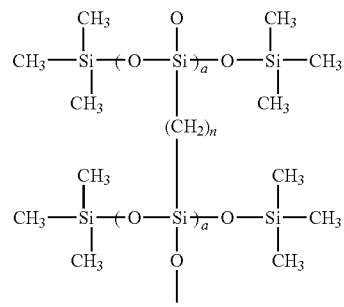

In the case where n=1 acetylene is used as a crosslinking reactant. It is reacted with a silanic hydrogen polymer. As n is increased the reactant is an alpha omega divinyl compound.

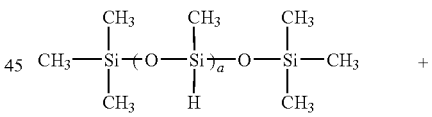

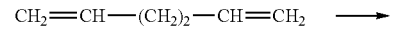

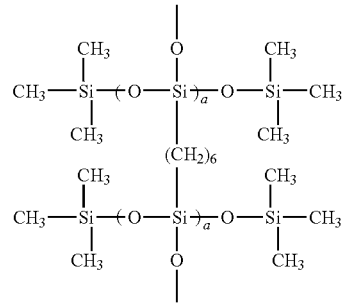

The reaction is called hydrosilylation and provides the linking groups between the molecules. The reaction is generally run in solvent like cyclomethicone (D4 or D5 or hexamethyl disiloxane) or in volatile organic like isododecane. A catalyst generally a platinum one is used to effect the reaction. Chloroplatinic acid or Karnsteadt catalyst are preferred. The resulting material is a viscous liquid that when the solvent evaporates provides a film.

The present invention makes use of novel crosslinking reagents that provide groups that significantly alter the solubility of the resin. This is done by introducing fatty ester linkages, water soluble groups linked with fatty esters and glyceryl esters. Not only does the solubility change, the ability to formulate solid products free from syneresis also occurs. Another unexpected benefit is that the ester moiety provides improved biodegradation of the resin making the resin "more green" and improving consumer acceptability. None of these advantageous are present in the compounds known heretofore.

THE INVENTION

Object of the Invention

It is the object of the present invention to provide a series of silicone polymers that make use of a unique crosslink compound. This compound is very efficient in reacting with a variety of silanic hydrogen containing polymers to provide a crosslinked product. The crosslinker is an undecylenic ester of dimer diol.

Another object of the present invention is to provide a series of products suitable for formulation into personal care products providing improved skin feel (i.e. not drying like Q resins) and having improved solubility over alkyl linked polymers.

Other objects of the invention will become clear as one reads the specification attached hereto.

All % given herein are % by weight, all temperatures are ° C., all patents and publications referred to herein are incorporated herein by reference in their entirety as appropriate.

SUMMARY OF THE INVENTION

The present invention relates to a series of silicone resins that (a) provide improved oil solubility and film forming properties when reacted into resin systems.

The compounds of the present invention are made by reacting specific vinyl diester compounds with silicone compounds that contain multiple silanic hydrogen (Si—H) groups. The reaction is conducted in a suitable solvent selected from the group consisting of cyclomethicone (D-4 and D-5 and mixtures thereof) and isoalkanes (iso-dodecane).

DETAILED DESCRIPTION OF THE INVENTION

Resins of the present invention are a class of silicone compounds which are prepared by the reaction of a poly-vinyl compound reacted with a silanic hydrogen containing compound.

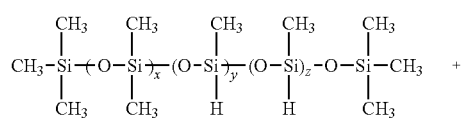  +

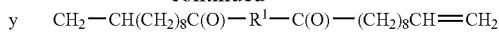

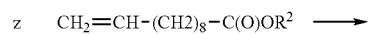

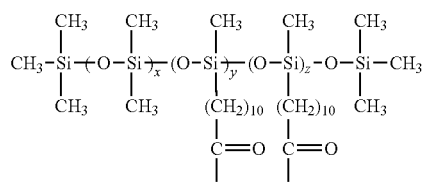

wherein;

$R^1$ is a mixture of:

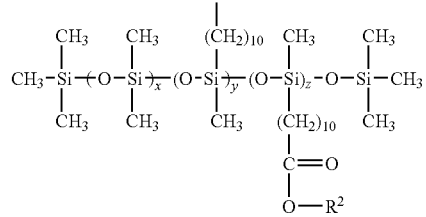

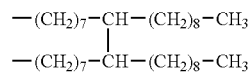

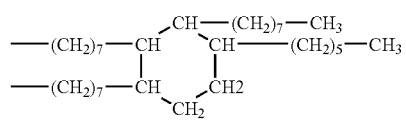

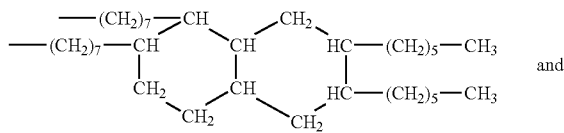

and

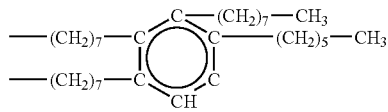

wherein:

$R^2$ is alkyl having 8 to 36 carbon atoms;

x is an integer ranging from 0 to 2000;

y is an integer ranging from 2 to 200;

z is an integer ranging from 0 to 200;

e is an integer ranging from 6 to 35;

f is an integer ranging from 0 to 20;

g is an integer ranging from 0 to 20;

h is an integer ranging from 0 to 20.

The reactions are typically carried out in a solvent, either volatile silicone (cyclomethicone (D4 or D5 or mixtures thereof) or hydrocarbon solvent like isododecane. A suitable hydrosilylation catalyst like chloroplatinic acid or Karnstedt catalyst are used.

The value of "y" determines the degree of crosslinking and consequently if the product is resinous or elastomeric. Elastomeric materials are compounds that are crosslinked to a lesser extent than resins. They are "rubbery" producing films that are rubber band like. Resins in contrast are not rubbery, but are hard and because of their higher crosslink density form powders when struck by a hammer.

We have also found that reaction of an undecylenate ester will allow for the incorporation of the "R" moiety onto the molecule thereby increasing oil solubility and compatibility with oily materials present in the personal care application.

Crosslinker

We have surprisingly and unexpectedly found that the undecylenate di-ester of dimol alcohol is a surprisingly good crosslinker when making silicone resins.

Dimol alcohol is a commercially available di-alcohol. It is available from a variety of sources including Jarchem located in Newark, N.J. It is a mixture of products conforming to the following structures:

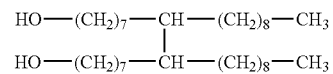

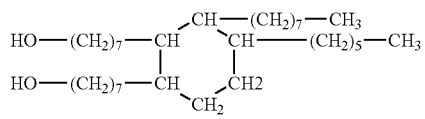

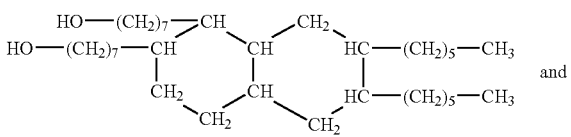

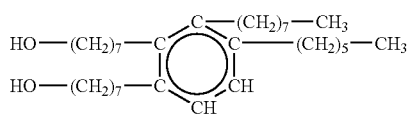

and

This crosslinker is made by the reaction of two moles of undecylenic acid to form a mixed alpha-omega di vinyl crosslinker. Undecylenic acid is an item of commerce. The crosslinker conforms to the following structure:

$$CH_2=CH-(CH_2)_8C(O)-O-(CH_2)_7-CH-(CH_2)_8-CH_3$$
$$CH_2=CH-(CH_2)_8C(O)-O-(CH_2)_7-CH-(CH_2)_8-CH_3$$

$$CH_2=CH-(CH_2)_8C(O)-O-(CH_2)_7-CH\begin{array}{c}CH-(CH_2)_7-CH_3\\CH-(CH_2)_5-CH_3\\CH_2\end{array}$$
$$CH_2=CH-(CH_2)_8C(O)-O-(CH_2)_7-CH\begin{array}{c}\\CH_2\end{array}$$

and

The undecylenic acid esters are one aspect of the present invention. The product is made by an esterification reaction which is carried out at temperatures of between 150° C. and 220° C. Esterification catalysts can be added as required.

The second reactant is a silanic hydrogen containing compound, which is an item of commerce commercially available from Siltech LLC, Dacula, Ga., conforming to the following structure:

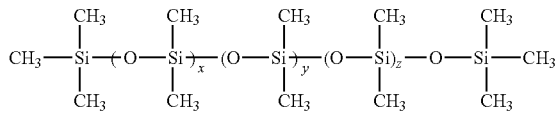

An optional material (when "z" is not zero), is a fatty ester of undecylenic acid. This reactant is made by the reaction of a fatty alcohol with undecylenic acid.

The reaction is as follows:

$R^2$—OH+$CH_2$=CH—$(CH_2)_8$—C(O)OH->$R^2$O—C(O)—$(CH_2)_8$—CH=$CH_2$+$H_2O$

The reaction is carried out using commercially available raw materials including undecylenic acid and fatty alcohols at temperatures of between 150° C. and 220° C. Esterification catalysts can be added as required The addition of this material to the reaction mixture results in increased ester groups and increases compatibility with organics used in the formulation of pigmented products.

Resins with improved compatibility with organic components has been a long felt unsatisfied need in the personal care area.

The present invention relates to a series of compounds made by the hydrosilylation reaction of a silanic hydrogen containing silicone conforming to the following structure:

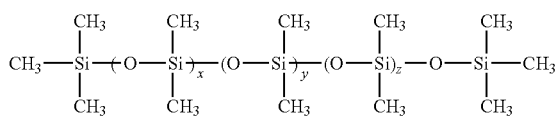

wherein;
x is an integer ranging from 0 to 2000;
y is an integer ranging from 2 to 200;
z is an integer ranging from 0 to 200;
e is an integer ranging from 6 to 35;
f is an integer ranging from 0 to 20;
g is an integer ranging from 0 to 20;
h is an integer ranging from 0 to 20;

with an alpha-omega diol compound which is a mixture conforming to the following structures;

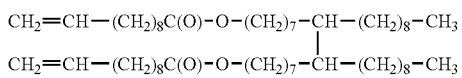

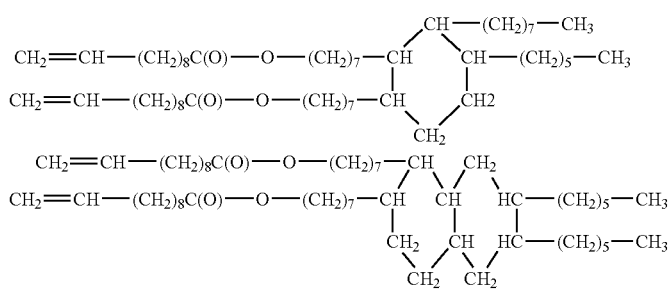

and

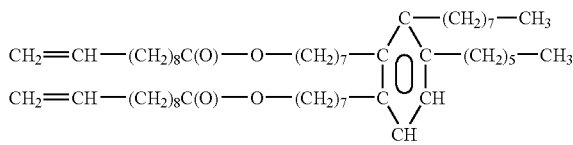

and optionally a mono substituted undecylenic compound conforming to the following structure:

$R^2$O—C(O)—$(CH_2)_8$—CH=$CH_2$ wherein;

$R^2$ is alkyl having 8 to 36 carbon atoms;

in the presence of a suitable hydrosilylation catalyst;

in a suitable volatile solvent selected from the group consisting of cyclomethicone, hexamethyldisiloxane and isoparaffin.

Another aspect of the present invention relates to a series of compounds made by the hydrosilylation reaction conforming to the following structure:

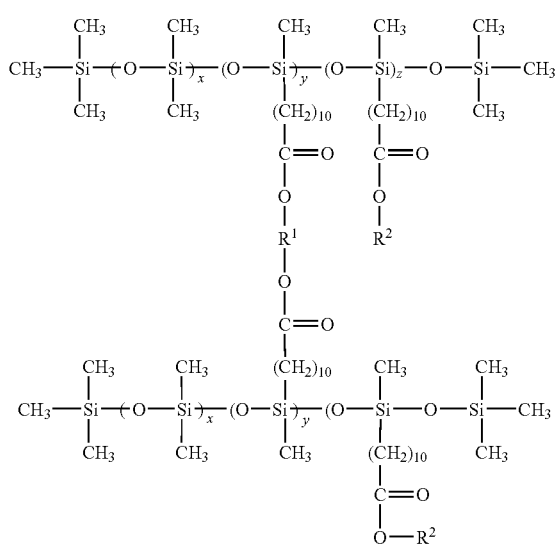

wherein;

$R^1$ is a mixture of:

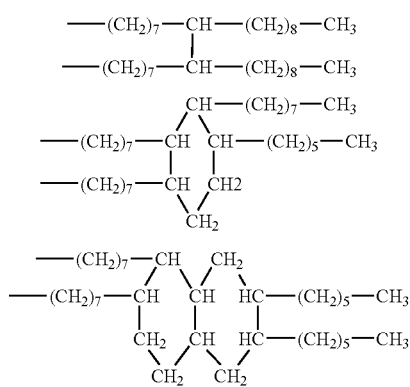

and

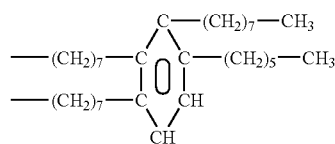

wherein:

$R^2$ is alkyl having 8 to 36 carbon atoms;

x is an integer ranging from 0 to 2000;

y is an integer ranging from 2 to 200;

z is an integer ranging from 0 to 200;

e is an integer ranging from 6 to 35;

f is an integer ranging from 0 to 20;

g is an integer ranging from 0 to 20;

h is an integer ranging from 0 to 20.

PREFERRED EMBODIMENTS

In a preferred embodiment z is 0.

In a preferred embodiment z ranges from 1 to 20.

In a preferred embodiment $R^2$ is alkyl having 12 carbon atoms.

In a preferred embodiment $R^2$ is alkyl having 14 carbon atoms.

In a preferred embodiment $R^2$ is alkyl having 16 carbon atoms.

In a preferred embodiment $R^2$ is alkyl having 18 carbon atoms

In a preferred embodiment $R^2$ is alkyl having 20 carbon atoms

In a preferred embodiment $R^2$ is alkyl having 22 carbon atoms.

In a preferred embodiment $R^2$ is alkyl having 24 carbon atoms

In a preferred embodiment $R^2$ is alkyl having 36 carbon atoms.

EXAMPLES

Raw Materials

Example 1

Undecylenic Acid

Undecylenic acid is an item of commerce available from a variety of sources. It conforms to the following structure:

$CH_2=CH-(CH_2)_8-C(O)OH$

Example 2

Dimol Alcohol

Dimol alcohol is a commercially available di-alcohol. It is available from a variety of sources including Jarchem located in Newark, N.J. It is a mixture of products conforming to the following structures:

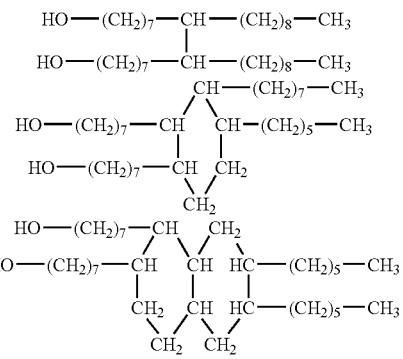

and

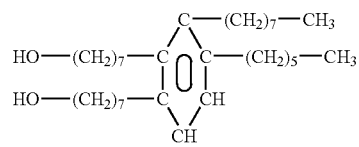

Examples 3-14

Fatty Alcohols

Fatty Alcohols are items of commerce. They conform to the following structure:

$R^2OH$

| Example | $R^2$ Formula |
| --- | --- |
| 3 | $C_8H_{17}$ |
| 4 | $C_{10}H_{21}$ |
| 5 | $C_{12}H_{25}$ |
| 6 | $C_{14}H_{29}$ |
| 7 | $C_{16}H_{33}$ |
| 8 | $C_{18}H_{37}$ |
| 9 | $C_{20}H_{41}$ |
| 10 | $C_{22}H_{45}$ |

-continued

| Example | R² Formula |
|---------|------------|
| 11 | $C_{24}H_{49}$ |
| 12 | $C_{36}H_{73}$ |
| 13 | $C_{26}H_{53}$ |
| 14 | $C_{30}H_{61}$ |

Silanic Hydrogen Silicone Compounds

Examples 15-25

Silanic Hydrogen compounds are items of commerce made by a variety of suppliers, including Siltech Corporation in Toronto Canada. They conform to the following structure:

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_x-(O-\underset{\underset{H}{|}}{\overset{\overset{CH_3}{|}}{Si}})_y-(O-\underset{\underset{H}{|}}{\overset{\overset{CH_3}{|}}{Si}})_z-O-\underset{\underset{CH_3}{|}}{\overset{\overset{CH_3}{|}}{Si}}-CH_3$$

wherein;

x is an integer ranging from 0 to 2000;
y is an integer ranging from 2 to 200;
z is an integer ranging from 0 to 200;
e is an integer ranging from 6 to 35;
f is an integer ranging from 0 to 20;
g is an integer ranging from 0 to 20;
h is an integer ranging from 0 to 20.

| Example | x | y | z |
|---------|------|-----|-----|
| 15 | 0 | 2 | 0 |
| 16 | 10 | 5 | 20 |
| 17 | 15 | 20 | 15 |
| 18 | 25 | 50 | 9 |
| 19 | 50 | 25 | 50 |
| 20 | 75 | 15 | 0 |
| 21 | 100 | 28 | 5 |
| 22 | 5 | 5 | 15 |
| 23 | 10 | 150 | 10 |
| 24 | 6 | 100 | 200 |
| 25 | 2000 | 200 | 0 |

Crosslinker Preparation

General Procedure

The crosslinkers are made by the esterification reaction of undecylenic acid and a variety of hydroxy containing compounds.

To 184.0 grams of undecylenic acid (Example 1) is added the specified number of grams of the specified hydroxy containing compound (Examples 2-14). A catalyst is recommended, although the reaction can be run without one. Preferred catalyst is stannous oxylate. The reaction mixture is heated to 150-200° C. Water will distill off as reaction proceeds. The amount of water distilled off is measured and used to monitor the reaction. The reaction is also monitored by acid value reduction.

| | Hydroxy Compound | |
|---------|---------|-------|
| Example | Example | Grams |
| 26 | 2 | 268 |
| 27 | 3 | 130 |
| 28 | 4 | 158 |
| 29 | 5 | 186 |
| 30 | 6 | 214 |
| 31 | 7 | 242 |
| 32 | 8 | 270 |
| 33 | 9 | 298 |
| 34 | 10 | 326 |
| 35 | 11 | 354 |
| 36 | 12 | 522 |
| 37 | 13 | 382 |
| 38 | 14 | 438 |

Hydrosilylation Compounds of the Present Invention

Hydrosilylation Solvents

Examples 39-42

The hydrosilylation reactions are advantageously run in a volatile solvent, which can later be distilled off is desired. It is also a practice to sell the products in solvent.

| Example | Description |
|---------|-------------|
| 39 | isododecane |
| 40 | cyclomethicone |
| 41 | isodecane |

Hydrosilylation

Hydrosilylation is a process that reacts terminal vinyl compounds with silanic hydrogen to obtain a Si—C bond. References to this reaction, incorporated herein by reference, include:

U.S. Pat. Nos. 3,715,334 and 3,775,452 to Karstedt, shows the use of Pt(O) complex with vinylsilicon siloxane ligands as an active hydrosilylation catalyst.

Additional platinum complexes, such as complexes with platinum halides are shown by, U.S. Pat. No. 3,159,601 Ashby and, U.S. Pat. No. 3,220,972, to Lamoreaux.

Another hydrosilylation catalyst is shown by Fish, U.S. Pat. No. 3,576,027. Fish prepares a platinum(IV) catalyst by reacting crystalline platinum(IV) chloroplatinic acid and organic silane or siloxane to form a stable reactive platinum hydrosilylation catalyst.

General Procedure

To the specified number of grams of the specified solvent (Examples 39-41) is added the specified number of grams of the specified silanic hydrogen compound (Example 15-25). The mass is mixed well. To that mixture is added the specified number of grams of the specified dimol undecylenate (Example 26) compound and the specified number of grams of the monosubstituted undecylenate esters (Examples 27-38). The reaction mass is mixed well until homogeneous. To that mixture is added 0.01% Karstedt catalyst, which is commercially available from Geleste. The agitation is stopped and the reaction begins with an exotherm. The reaction mass will thicken over 4 hours, but most rapidly in the first twenty minutes. Once the maximum viscosity is reached the reaction is considered complete. The solvent may be distilled off or the product may be sold as prepared without additional purification.

Polymers

Examples 42-67

Example 26

| | | | | | | | |
|---|---|---|---|---|---|---|---|
| Diol Ester | | Silanic Hydrogen | | Mono-Vinyl | | Solvent | |
| Example | Grams | Example | Grams | Example | Grams | Example | Grams |
| 42 | 867 | 15 | 284 | — | 0 | 39 | 11510 |
| 43 | 216 | 16 | 240 | 26 | 53 | 39 | 5107 |
| 44 | 867 | 17 | 337 | 27 | 195 | 39 | 13994 |
| 45 | 2167 | 18 | 555 | 28 | 142 | 39 | 9141 |
| 46 | 1083 | 19 | 836 | 29 | 930 | 39 | 2849 |
| 47 | 650 | 20 | 661 | — | 0 | 39 | 6508 |
| 48 | 1213 | 21 | 64 | 31 | 121 | 39 | 13994 |
| 49 | 2168 | 22 | 1734 | 32 | 4050 | 39 | 7500 |
| 50 | 650 | 23 | 105 | 33 | 29 | 39 | 1354 |
| 51 | 4335 | 24 | 1860 | 35 | 708 | 39 | 69038 |
| 52 | 867 | 25 | 1601 | — | 0 | 39 | 24686 |
| 53 | 216 | 16 | 240 | 37 | 764 | 39 | 24436 |
| 54 | 867 | 17 | 337 | 38 | 657 | 39 | 23267 |
| 55 | 867 | 15 | 284 | — | 0 | 40 | 11510 |
| 56 | 216 | 16 | 240 | 26 | 536 | 41 | 9932 |
| 57 | 867 | 17 | 337 | 27 | 1950 | 40 | 31540 |
| 58 | 216 | 18 | 55 | 28 | 14 | 40 | 2865 |
| 59 | 108 | 19 | 83 | 29 | 93 | 40 | 34380 |
| 60 | 65 | 20 | 66 | — | 0 | 41 | 1310 |
| 61 | 121 | 21 | 6 | 30 | 10 | 41 | 1360 |
| 62 | 216 | 22 | 173 | 32 | 405 | 40 | 7952 |
| 63 | 650 | 23 | 105 | 33 | 29 | 40 | 7840 |
| 64 | 433 | 24 | 186 | 35 | 708 | 41 | 13275 |
| 65 | 867 | 25 | 1601 | — | 0 | 41 | 6404 |
| 66 | 216 | 16 | 240 | 37 | 764 | 41 | 12000 |
| 67 | 86 | 17 | 33 | 38 | 65 | 40 | 1861 |

The key to understanding the functionality of the resin of the present invention is an appreciation that silicone and oil are mutually immiscible groups. This lack of solubility is the cause of the syneresis (or separation) seen in pigmented products that contain oil, and silicone. If the molecule has these groups properly connected the molecule will orientate itself into the lowest free energy. In this configuration the oil loving and silicone portions of the resin and of the formulation will all associate in a matrix. The parts of this linking group that connect to the silicone group are oil soluble. The length of that group is fairly long and symmetrical. The internal group is water loving (polar). Resins with this configuration allows for the incorporation of both oil loving (non-polar non-silicone) and silicone loving components in the formulation. This produces an emollient property to the skin in a film forming matrix. The presence of the ester group helps biodegradability.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

I claim:

1. A silicone polymer conforming to the following structure;

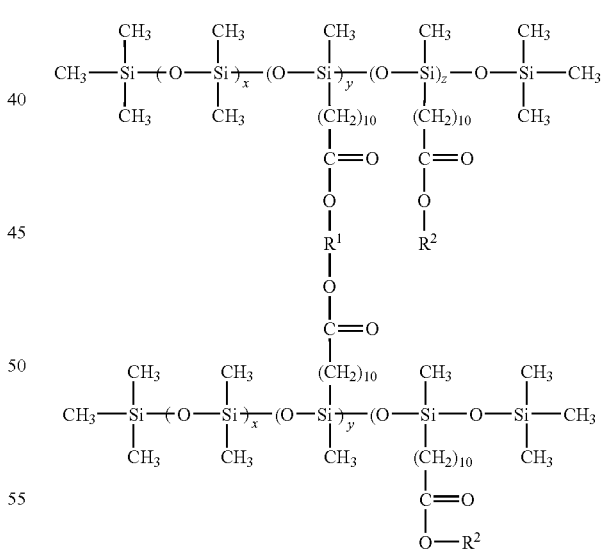

wherein;

$R^1$ is a mixture of:

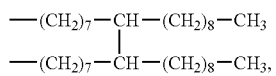

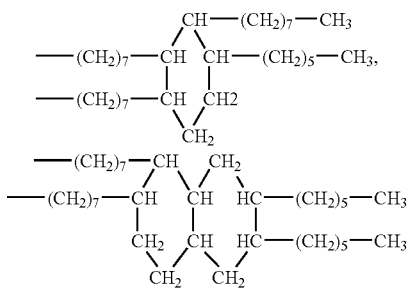

and

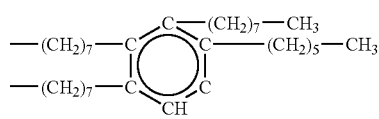

wherein:
R² is alkyl having 8 to 36 carbon atoms;
x is an integer ranging from 0 to 2000;
y is an integer ranging from 2 to 200;
z is an integer ranging from 0 to 200.

2. A silicone polymer of claim 1 wherein z is 0.
3. A silicone polymer of claim 1 wherein z ranges from 1 to 20.
4. A silicone polymer of claim 1 wherein R² is alkyl having 12 carbon atoms.
5. A silicone polymer of claim 1 wherein R² is alkyl having 14 carbon atoms.
6. A silicone polymer of claim 1 wherein R² is alkyl having 16 carbon atoms.
7. A silicone polymer of claim 1 wherein R² is alkyl having 18 carbon atoms.
8. A silicone polymer of claim 1 wherein R² is alkyl having 20 carbon atoms.
9. A silicone polymer of claim 1 wherein R² is alkyl having 22 carbon atoms.
10. A silicone polymer of claim 1 wherein R² is alkyl having 24 carbon atoms.
11. A silicone polymer of claim 1 wherein R² is alkyl having 36 carbon atoms.
12. The silicone polymer of claim 1 made by the hydrosilylation reaction of a silanic hydrogen containing silicone conforming to the following structure:

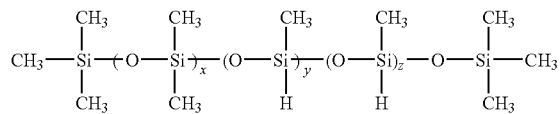

x is an integer ranging from 0 to 2000;
y is an integer ranging from 2 to 200;
z is an integer ranging from 0 to 200;
and
a dimol undecylenate which is a mixture of conforming to the following structure:

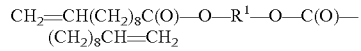

wherein;
R¹ is a mixture of:

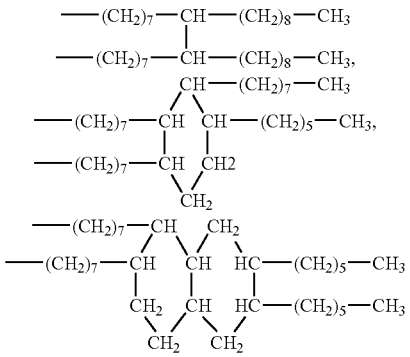

and

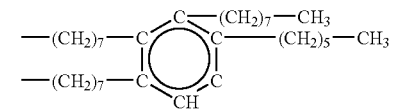

and optionally a monosubstituted undecylenate ester conforming to the following structure:

R² is alkyl having 8 to 36 carbon atoms.
13. A silicone polymer of claim 12 wherein z is 0.
14. A silicone polymer of claim 12 wherein z ranges from 1 to 20.
15. A silicone polymer of claim 12 wherein R² is alkyl having 12 carbon atoms.
16. A silicone polymer of claim 12 wherein R² is alkyl having 14 carbon atoms.
17. A silicone polymer of claim 12 wherein R² is alkyl having 16 carbon atoms.
18. A silicone polymer of claim 12 wherein R² is alkyl having 18 carbon atoms.
19. A silicone polymer of claim 12 wherein R² is alkyl having 20 carbon atoms.
20. A silicone polymer of claim 12 wherein R² is alkyl having 22 carbon atoms.

* * * * *